(12) United States Patent
Hunsley et al.

(10) Patent No.: US 12,235,258 B2
(45) Date of Patent: Feb. 25, 2025

(54) FLOAT ANGLE PROBES FOR MONITORING WELLBORE FLUID COMPOSITION AND METHODS OF USING THE SAME

(71) Applicant: Newpark Drilling Fluids LLC, The Woodlands, TX (US)

(72) Inventors: Kendra Hunsley, Calgary (CA); Jesse Hubbard, Millarville (CA); Blair Lillejord, Chestermere (CA)

(73) Assignee: Newpark Drilling Fluids LLC, The Woodlands, TX (US)

( * ) Notice: Subject to any disclaimer, the term of this patent is extended or adjusted under 35 U.S.C. 154(b) by 122 days.

(21) Appl. No.: 18/056,209

(22) Filed: Nov. 16, 2022

(65) Prior Publication Data
US 2023/0160871 A1 May 25, 2023

Related U.S. Application Data

(60) Provisional application No. 63/282,237, filed on Nov. 23, 2021.

(51) Int. Cl.
*G01N 9/00* (2006.01)
*G01F 23/64* (2006.01)
*G01N 33/28* (2006.01)

(52) U.S. Cl.
CPC ............ *G01N 33/28* (2013.01); *G01F 23/64* (2013.01); *G01N 9/00* (2013.01)

(58) Field of Classification Search
CPC ............ G01N 33/28; G01N 9/00; G01N 9/10; G01N 9/12; G01N 9/16; G01N 33/2823; G01F 23/64; G01F 23/68; E21B 21/01; E21B 47/04

USPC ....... 73/19.09, 32 R, 444–454, 53.01, 61.41, 73/61.51, 152.04–152.6, 305, 309, 313, 73/314; 175/40, 48; 166/250.01, 252.3, 166/250.05

See application file for complete search history.

(56) References Cited

U.S. PATENT DOCUMENTS

| | | | | |
|---|---|---|---|---|
| 4,474,254 | A * | 10/1984 | Etter ...................... | E21B 21/06 366/136 |
| 8,766,641 | B2 * | 7/2014 | Pindiprolu ............. | G01N 13/00 166/250.01 |
| 2005/0257631 | A1 * | 11/2005 | Mayeaux ............. | G01N 1/2247 73/864.62 |
| 2014/0260607 | A1 * | 9/2014 | Baron ..................... | G01N 9/12 73/448 |

(Continued)

FOREIGN PATENT DOCUMENTS

GB 2202047 * 9/1988

*Primary Examiner* — Robert R Raevis
(74) *Attorney, Agent, or Firm* — Vorys, Sater, Seymour and Pease LLP

(57) ABSTRACT

A method includes conveying a wellbore fluid into a container of a wellsite system, the container having a float angle hydrometer housed therein and the float angle hydrometer including a buoyant structure, and a measuring component housed within or attached to the buoyant structure. The method further includes determining one or more fluid properties of the wellbore fluid with the float angle hydrometer based on an inclination of the buoyant structure within the wellbore fluid, the one or more fluid properties including at least one of density, specific gravity, or fluid level.

16 Claims, 2 Drawing Sheets

(56) References Cited

U.S. PATENT DOCUMENTS

2020/0128078 A1\* 4/2020 Cyca ...................... G01K 13/02
2022/0234010 A1\* 7/2022 Abughaban ......... B01F 35/2136

\* cited by examiner

FLOAT ANGLE PROBES FOR MONITORING WELLBORE FLUID COMPOSITION AND METHODS OF USING THE SAME

BACKGROUND OF THE DISCLOSURE

Wellbore operations in geological formations involve the management of large volumes of wellbore fluids. During drilling, wellbore fluids, such as a drilling fluid or "mud," is circulated downhole to perform various tasks including lubricating the drill bit, transportation of drill cuttings, and maintenance of hydrostatic pressure against the formation. As the wellbore fluid is continually pumped downhole, displaced fluids return to the surface along with entrained solids, gases, and connate fluids encountered downhole.

The material accumulated downhole can change the properties of the wellbore fluid, which can result in changes to operational performance. In the case of drilling performance, accumulated materials in the fluids can cause reduced rate of penetration, downhole mud losses and filter cake buildup beyond an optimal amount. In addition, wellbore fluids can begin to exhibit corrosive properties during drilling and production operations. Corrosive gases, such as $H_2S$ and $CO_2$ may become entrained in the fluid, which can degrade both surface and downhole equipment, particularly those components made of carbon steel. Additionally, accumulated abrasive particulates may deteriorate the equipment, which can lead to reduced equipment performance and eventual failure. Degraded performance and unexpected equipment failure can lead to undesirable operational downtime and additional costs incurred to repair equipment.

Further, adverse changes in wellbore fluid composition can affect the quality of the wellbore resulting in operational difficulties. Examples include unwanted changes in wellbore fluid density resulting in an increase to well cave-in potential, which could lead to stuck pipe and/or drill bit sticking. Such difficulties will likely result in increased operational time and a subsequent cost increase. Poor wellbore quality may also affect an overall reduction in the yield of the well.

To mitigate changes in wellbore fluid composition that can impact performance, wellbore fluids are collected upon return to the well surface and reconditioned in stages to remove contaminants, including solids, fines, and gases. Wellbore fluids can also be treated with additives to remove emulsions and flocculate solids, and to replenish brines and other fluids or additives that may have been depleted downhole or removed with unwanted contaminants at surface. Treated fluids are then transferred back to suction tanks to be circulated downhole. Wellbore fluid reconditioning requires analysis of fluid properties to identify the presence of contaminants, and to verify that reconditioning methods are effective in maintaining fluid characteristics within desired performance limits.

Traditional wellbore fluid measurement techniques involve manual sampling, often at inconsistent time intervals, in laboratories that are onsite or remote. Other conventional methods include the use of specialized equipment integrated into downhole equipment. Each of the aforementioned methods require the need to mobilize specialized vehicles and/or other large equipment as well as crews of technicians to a wellsite. Enablement of equipment and crews to remote wellsites increases both costs and delays in obtaining needed data.

Thus, there is a need for improved fluid monitoring and fluid property measurement devices capable of monitoring wellbore fluids within a surface wellbore fluid circulating system in real-time to track changes in fluid composition during wellbore operations.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

Figure 1:
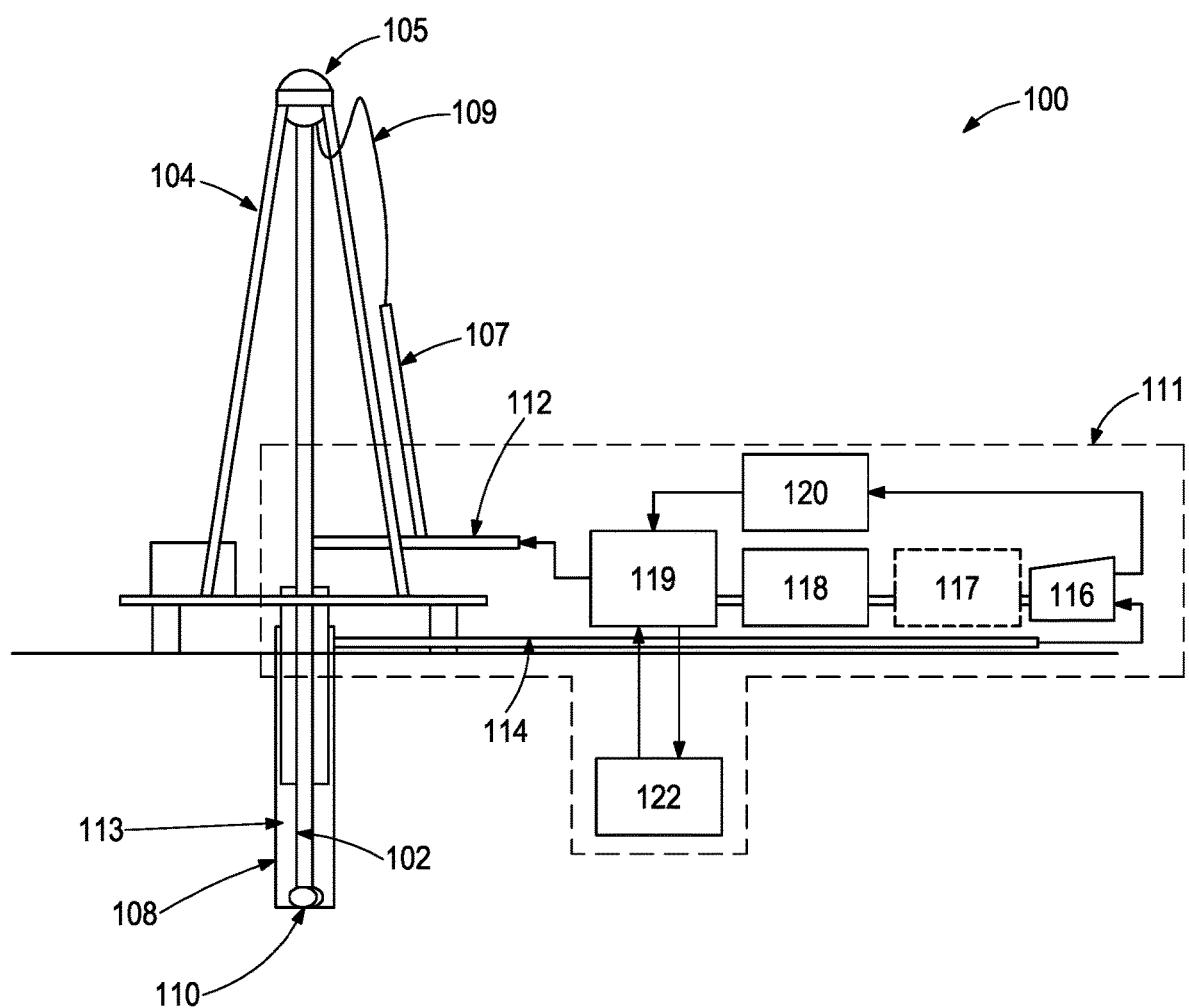
FIG. 1 is a schematic diagram of an example wellsite that may incorporate the principles of the present disclosure.

The present disclosure is related to the real-time monitoring of wellbore fluids utilized during wellbore operations and, more particularly, to measuring fluid compositions by means of a float angle hydrometer located within a surface wellbore circulating system.

Embodiments of the present disclosure describe systems and methods of using a float angle hydrometer to measure wellbore fluid composition in order to monitor, maintain and adjust fluid properties to optimize overall well performance. Methods disclosed herein include monitoring wellbore fluid composition and obtaining instantaneous and/or real-time feedback of a number of fluid properties, including but not limited to wellbore fluid density, specific gravity, and fluid level. For example, a float angle hydrometer may be used to monitor wellbore fluid density that may be affected by components such as ions, solids, phases, and the like. Fluid density can have a critical affect upon hydrostatic pressure, fluid suspension properties, and ultimately wellbore stability. As such, critical monitoring of fluid properties such as density is essential to the overall success of the well. Subsequently, methods disclosed herein may include performing remedial action to modify wellbore fluid properties including but not limited to, fluid density.

Systems disclosed herein include a float angle hydrometer that may be included in an existing surface wellbore fluid circulating system. The float angle hydrometer may be portable, modular and may be combined with other probe measurement apparatuses (capable of measuring fluid properties, such as wellbore fluid density, specific gravity, fluid level, oxygen level, pH, conductivity, and the like) to provide a holistic representation of the wellbore fluid throughout an operation. Measurement tanks disclosed herein may contain standard components (e.g., pumps, drainage valves, overflows, etc.) that draw wellbore fluids from an associated tank, such as a mud tank.

The surface wellbore fluid circulating systems described herein may incorporate a discrete and dedicated measurement tank in fluid connection with, but separate from, other functional tanks of the circulating system, such as mud and/or surge tanks. A dedicated measurement tank provides for easier installation and maintenance of a float angle hydrometer. Wellbore fluids captured within the dedicated measurement tank enable measurements in a more controlled environment, minimizing errors caused by excessive turbulence commonly associated with the use of agitators or wash guns elsewhere in the circulating system.

Surface-located float angle hydrometers may be used to provide wellbore fluid property data without the need for downhole measurements or the use of expensive specialized equipment designed to withstand downhole operating conditions. Additionally, a float angle hydrometer that provides continuous real-time measurements eliminates the need for and inconsistency of manual sampling. Real-time measurements allow for real-time monitoring of wellbore fluids and faster remedial response. As such, the methods described herein may help to enhance overall wellbore quality, increase efficiency, and reduce cost.

FIG. 1 is an isometric view of an example wellsite 100 that may incorporate the principles of the present disclosure. As illustrated, the wellsite 100 includes a drilling derrick 104 positioned atop a wellbore 108 that extends below the Earth's surface. The wellsite further includes a surface wellbore fluid circulating system 111, which may include a series of fluid handling tanks and/or pits that filter, process and redirect wellbore fluids used at the wellsite, as needed. In some embodiments, as illustrated, the surface wellbore fluid circulating system 111 (hereafter "the circulating system 111") includes a fluid separation system 116, a first settling tank 117, a second settling tank 118, a suction tank 119, a flocculation tank 120, and a measurement tank 122.

The wellsite 100 may be used to conduct drilling operations to extend the length of the wellbore 108. During the drilling operation, a wellbore fluid (alternately referred to as "drilling mud" or "mud") is pumped by means of a mud pump (not shown) from the suction tank 119 through a mud supply line 112, up a standpipe 107, through a high pressure hose 109, and into to a swivel connector 105. In some embodiments, the swivel connector 105 may be operatively coupled to a kelly rig rotating system. In other embodiments, the high pressure hose 109 may be operatively connected to a top drive power swivel in conjunction with a rig utilizing a top drive rotating system.

The swivel connector 105 is operatively and fluidly coupled to a drill string 102 such that the wellbore fluid (drilling mud) may be pumped down the drill string 102 to a drill bit 110 arranged at the distal end of the drill string 102. The wellbore fluid exits through nozzles provided on the drill bit 110 and then proceeds back up through annular space 113 defined between the drill string 102 and the inner wall of the wellbore 108. The wellbore fluid exits the wellbore 108 by means of a mud return line 114 and re-enters the circulating system 111.

As briefly mentioned above, the circulating system 111 may include a configuration of fluid handling tanks and/or pits that filter and process the wellbore fluid, ultimately redirecting the wellbore fluids back into the drill string 102 and the wellbore 108. Circulation of the wellbore fluid is continuous through the closed loop system until drilling operations are complete. Once drilling operations are completed, spent wellbore fluids may be redirected to storage or disposal tanks.

As the wellbore fluid returns to the surface, the mud return line 114 directs the wellbore fluid to the fluid separation system 116, which may include one or more shakers or similar devices to remove solids (alternatively referred to as "cuttings") and fines from the wellbore fluid. The fluid separation system 116 may include other solids control equipment in addition to or instead of shakers, such as desanders, desilters, screens, centrifuges, cuttings dryers, electrophoresis, vacuums, or combinations thereof. After solids removal, the wellbore fluid is transferred to a settling tank. In some embodiments, the circulating system 111 includes the first and second settling tanks 117, 118, but could alternatively only include the first settling tank 117, without departing from the scope of the disclosure. In such embodiments, the second settling tank 118 may be omitted. Configuration of the circulating system 111 will be dependent upon the specific needs of the well for solid separation and wellbore fluid reconditioning.

In some embodiments, as illustrated in FIG. 1, at least a portion of the wellbore fluid may be transferred from the fluid separation system 116 to a flocculation tank 120, where the wellbore fluid is reconditioned with flocculants, as needed. Flocculants are a chemical agent that assists in the aggregation of fine grained solids, increasing solid settling volume and ultimately aiding in solids removal from the wellbore fluid. In some embodiments, the flocculation tank 120 may be utilized for the addition of other additives to remove entrained solids and contaminants. In some embodiments, after flocculation, the wellbore fluid may be discharged back into the first settling tank 117 (pathway not shown) to allow more settling time. Alternatively, the wellbore fluid exiting the flocculation tank 120 may be directed into the suction tank 119. Routing the wellbore fluid directly to the suction tank 119 shortens the volumes of the circulating system 111 and minimizes treatable volumes of the wellbore fluid.

In some embodiments, gaseous contaminants present downhole may become entrained in the wellbore fluids and require removal. In such embodiments, gas may be removed utilizing one or more degassers (not shown), such as vacuum degassers, and similar equipment. In such embodiments, once solids and gas are removed, the wellbore fluid flows from the settling tank(s) (e.g., the second settling tank 118) or the flocculation tank 120 (depending upon the wellsite 100 specific configuration of the circulating system 111) through the suction tank 119 and then back into the mud supply line 112 for recirculation through the entirety of the closed loop system.

Additionally, wellbore fluids may also be removed from the circulating system 111 entirely. For example, a portion of the wellbore fluids can be collected and transferred to a storage tank or pit (not shown) for reclamation or disposal.

FIG. 1 is provided as an example only, and it is envisioned that devices and methods of the present disclosure can be adapted to other configurations and for different wellbore operations, including completions, fracturing, and interventions. In some embodiments, devices of the present disclosure can be employed in wellbore operations having a variable number and type of tanks that can depend, for example, on the depth and type of wellbore. Wellbore operations can include the use of one or more settling or flocculation tanks, storage tanks, mixing tanks, and suction tanks arranged in any number of configurations.

During wellbore operations, wellbore fluids in the circulating system 111 may change in composition as gases, fluids and solids encountered downhole become entrained in the wellbore fluid. Similarly, the wellbore fluid composition may change as solids accumulated downhole are removed and as the wellbore fluid undergoes reconditioning and recirculation at surface. According to embodiments of the present disclosure, changes in composition and fluid properties may be monitored by placing one or more measurement probes in a tank or pit within the flow path of the circulating system 111, including positions within the suction tank 119, the first or second settling tank 117, 118, or the flocculation tank 120. Measurement probes may be configured to provide instantaneous and/or real-time measurements of properties of the wellbore fluid within the circulating system 111.

As illustrated in FIG. 1, systems and methods disclosed in the present embodiment, may utilize a discrete measurement tank 122 in fluid communication with wellbore fluids flowing through the circulating system 111. The measurement tank 122 provides a relatively stable measurement environment that is representative in fluid composition of the wellbore fluids in the circulating system 111. Utilization of the measurement tank 122 allows for the positioning of measurement probes such as a float angle hydrometer ("hydrometer"). The dedicated measurement tank 122 provides stable conditions for the hydrometer, whereas the hydrometer may otherwise be disturbed or damaged by flow, turbulence, foaming, or the presence of mechanical agitators such as augers, if positioned elsewhere within the circulating system 111. Further, placement of the hydrometer and/or probes within the discrete measurement tank 122 aids in reducing workplace hazards stemming from the need to manually place and remove probes from suction tanks and other vessels having actively moving mechanical parts.

In at least one embodiment, as shown in FIG. 1, the measurement tank 122 may be placed in fluid communication with the suction tank 119 to sample fluids prior to entry into the wellbore 108. In other embodiments, the measurement tank 122 may be placed at other locations in the circulating system 111. The measurement tank 122 may be placed directly in the flow path of the circulating system 111, for example, or in a diverted stream that actively or passively fills the measurement tank 122. Wellbore fluid may circulate continuously through the measurement tank 122, or fluids may be drawn into and evacuated from the measurement tank 122 as needed. In some embodiments, one or more valves may control flow into and out of the measurement tank 122, which may prove useful in providing isolation during measurement.

Fluid properties of the wellbore fluid may be measured in accordance with the present disclosure using a float angle hydrometer alone or in combination with one or more measurement probes placed in one or more locations in the circulating system 111. Float angle hydrometers may enable direct measurement of the wellbore fluid within a tank or container (e.g., the measurement tank 122), minimizing potential errors associated with manual sampling and transporting fluids. Moreover, due to their portability, float angle hydrometers provide a flexible platform for analyzing fluid conditions in one or more locations during wellbore operations. The float angle hydrometer can be placed at various locations in the circulating system 111 to optimize operational steps, such as solids concentrations and identification of changes in brine formulation.

Figure 2:
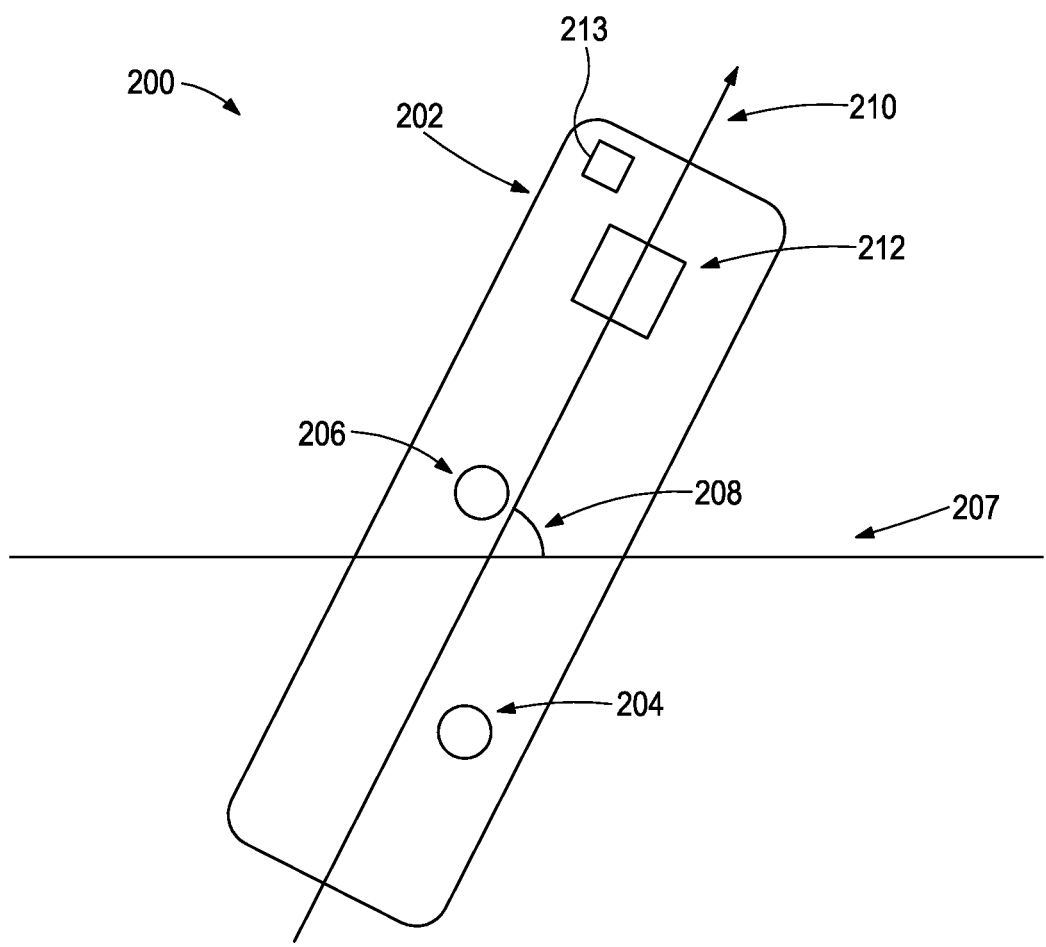
FIG. 2 is a schematic depicting a float angle hydrometer in accordance with the present disclosure.

FIG. 2 is a schematic side view of an example float angle hydrometer 200 that may be used in accordance with the principles of the present disclosure. The float angle hydrometer 200 (hereafter "the hydrometer 200") includes a buoyant housing 202 that encloses and protects the working components of the hydrometer 200 from the surrounding fluid. The hydrometer 200 may be a free-floating and self-contained device, or may be attached to a larger structure or array. The buoyant housing 202 may be made of any suitable material that protects the inner measurement components, such as plastics, metals, composites, and the like.

The hydrometer 200 is structured such that the center of gravity 204 and the center of buoyancy 206 are offset when placed in a fluid 207, e.g., the wellbore fluid. The difference between the center of gravity 204 and the center of buoyancy 206 causes the hydrometer 200 to react to the buoyant force of a fluid 207 by equilibrating at a characteristic inclination angle 208, defined by the surface of fluid 207 and a central axis 210 of the housing 202. The inclination angle 208 is proportional to the density of the fluid 207 and when calibrated with samples of know density, may be used for real-time, in situ, and/or automated sampling. Additional details and operating principles of float angle probes are described, for example, in U.S. Pat. Nos. 9,234,828 and 10,495,506.

The hydrometer 200 also includes a measurement module 212 that measures the angle 208 that is proportional to the density of fluid 207. Data regarding the angle 208 may be converted to any usable metric, such as fluid density, specific gravity, ionic strength, solids concentration, and the like. In some embodiments, the hydrometer 200 may also provide for measurement of a fluid level within a vessel, such as the measurement tank 122 (FIG. 1). For example, the hydrometer 200 may be tethered to the measurement tank 122 at a fixed depth and as the fluid 207 level rises or falls, the measurement module 212 indicates the corresponding change in the angle 208. The measurement module 212 may utilize any suitable apparatus for calculating the angle 208, such as an accelerometer, a mechanical or digital measuring device, and the like.

The hydrometer 200 may also include any associated components required for the operation of the measurement module 212, including but not limited to a power source, a computer system for processing and storing measurements, and a transmitter for sending data. Additional components may be included within or external to, the buoyant housing 202. External components may be operatively connected to the buoyant housing 202 by means of wired or wireless interfaces.

The hydrometer 200 may transfer data by way of an onboard transmitter 213 housed within the buoyant housing 202. Data transfer may include wireless transmission to a computer system (not shown) present at the wellsite 100 (FIG. 1) or to a remote location by any suitable wired or wireless protocol. For example, measurements can be taken in real-time, sent to a cloud or remote computer system, and then processed to determine one or more fluid properties. In some embodiments, the transmitter 213 can have an onboard computer system that processes data captured from the measurement module 212 and/or stores the data on a non-transitory computer-readable medium. In an aspect, the transmitter 213 of the present disclosure can include commercially available wireless transmitters.

The hydrometer 200 may transmit data in real-time and/or at user defined (predetermined) intervals. Data transmitted from the float angle hydrometer 200 can be communicated as single or continuous ("real-time") measurements. In one embodiment, measurements may be obtained continuously for a selected time period. In other embodiments, measurements may be obtained intermittently at defined (predetermined0 intervals. Measurement intervals can range from about 0.1 seconds to about 24 hours (1 day). The rate of measurement intervals may be dependent upon the probe type and application requirements.

The hydrometer 200 may measure and record data using an onboard computer system in communication with the measurement module 212 or may transmit data to an external computer system for processing and/or display of results. Two components or subsystems may be communicatively coupled through a wired or wireless communication network, including but not limited to Ethernet, LAN, fiber optics, radio, microwaves, Bluetooth, satellite, and the like. Operation and use of such communication networks is well known to those of ordinary skill in the art and will, therefore, not be discussed in detail herein.

Data collected from the hydrometer 200 may be transferred by the transmitter 213 to a computer system present at the wellsite 100 (FIG. 1) or to a remote location that collects, processes, and displays data directly or through a secondary computer system such as a laptop or portable device. Computer systems of the present disclosure include personal computers (e.g., desktop or laptop), tablet computers, mobile devices (e.g., personal digital assistant (PDA) or Smartphone), servers (e.g., blade server or rack server), a network storage devices, or any other suitable computing device and may vary in size, shape, performance, functionality, and price.

Any necessary data processing can be performed locally (onsite) or by a remote or cloud-based computer system. Data captured from the hydrometer 200 can be recorded and analyzed by the computer system in real-time. Alternatively, computer analysis of the wellbore fluid properties can be performed at any point in time and may include the calculation of property changes over time. Computer systems can be programmed with instructions to perform various data manipulations including aggregating data from multiple probes (e.g., multiple hydrometers 200) and providing composite data, such as density, corrosion rates, and/or scaling rates.

Computer systems of the present disclosure can store data on any suitable computer-readable media that can include nonvolatile, hard-coded type media, such as read only memories (ROMs), or erasable, electrically programmable read only memories such as EEPROMs or flash memory; recordable type media, such as flash drives, memory sticks, and other types of appropriate memories; and transmission type media such as digital and analog communication links. For example, such media can include operating instructions, as well as instructions related to the apparatus and the method steps of the present disclosure and can operate on a computer system.

Measurements obtained from the hydrometer 200 may be used in conjunction with performance limits or thresholds, such as minimum and maximum wellbore fluid density, specific gravity, or fluid level, that may trigger notification to an operator when (or ideally before) wellbore fluid property alarm levels are reached. The hydrometer 200 may be used in conjunction with monitoring software that can include custom programs or commercially available packages. In an aspect, fluid properties collected over time can also be constructed as algorithms used to predictively determine when wellbore fluid reconditioning is needed or when operational issues are likely.

In some embodiments, the methods disclosed herein may be applied to a variety of wellbore fluids compositions that may include a base fluid and various additives. Base fluids may be single phase or multi-phase (direct emulsion or invert emulsion, for example) containing one or more aqueous fluids or non-aqueous fluids. Suitable base fluids include aqueous fluids such as natural or synthetically formulated brine, produced water, and sea water. Suitable salts in aqueous fluids may include lithium, ammonium, sodium, potassium, cesium, magnesium, calcium, or zinc cations, and chloride, bromide, iodide, formate, nitrate, acetate, cyanate, or thiocynate anions. Examples of suitable water-soluble salts that comprise the above-listed anions and cations include, but are not limited to, ammonium chloride, lithium bromide, lithium chloride, lithium formate, lithium nitrate, calcium bromide, calcium chloride, calcium nitrate, calcium formate, sodium bromide, sodium chloride, sodium formate, sodium nitrate, potassium chloride, potassium bromide, potassium nitrate, potassium formate, cesium nitrate, cesium formate, cesium chloride, cesium bromide, magnesium chloride, magnesium bromide, zinc chloride, and zinc bromide. Wellbore fluids may also be oil-based or non-aqueous, or be an emulsion containing a non-aqueous phase. Non-aqueous fluids may include natural or synthetic oils such as diesel oil; mineral oil; hydrogenated and unhydrogenated olefins including polyalpha olefins, linear and branch olefins and the like, polydiorganosiloxanes, siloxanes, or organosiloxanes, esters of fatty acids such as straight chain, branched and cyclical alkyl ethers of fatty acids; similar compounds known to one of skill in the art; and mixtures thereof.

In some embodiments, the hydrometer 200 may be calibrated to measure fluid properties in wellbore fluids having densities of about 6.5 ppg or more, about 8 ppg or more, about 11 ppg or more, or about 13 ppg or more. In some embodiments, float angle hydrometers may be calibrated to measure wellbore fluids having a density in a range of about 6.5 ppg to about 21 ppg, about 10 ppg to about 18 ppg, or about 11 ppg to about 18 ppg.

Applications

Methods of the present disclosure include the use of the hydrometer 200 to determine one or more fluid properties of a wellbore fluid present in the surface wellbore fluid circulating system 111 (FIG. 1). In one embodiment, the hydrometer 200 may be used to monitor various wellbore fluid qualities and the presence of adverse conditions including, but not limited to, variations in the wellbore fluid density beyond the pre-determined range of fluid densities. Additionally, monitoring of wellbore fluid properties may include a comparison of real-time measurements to measurements acquired previously in the same drilling interval. Alternatively or in addition to, wellbore fluid monitoring may include comparison of real-time hydrometer 200 readings to a database of previously acquired offset well data to determine whether and what remedial action is needed or should be recommended. In one embodiment, the hydrometer 200 data may be presented graphically, accompanied with notifications and guidance for remedial measures that may be employed.

Methods of the present disclosure include measuring one or more fluid properties of a wellbore fluid in a container (e.g., the flocculation tank 120, the suction tank 119, or the measurement tank 122 of FIG. 1, a pit, or other vessel) containing the wellbore fluid using the hydrometer 200, wherein the one or more fluid properties include at least one of density, specific gravity, and fluid level; determining a change in the one or more fluid properties of the wellbore fluid over a time interval; and taking a remedial action to change the one or more fluid properties. In an aspect, the step of measuring occurs at or adjacent to a location in which the wellbore fluid enters a wellbore 108 in the circulating system 111.

In some embodiments, the hydrometer 200 can be used in conjunction with other measurement probes and apparatuses for analyzing wellbore fluid properties. Additional measurements include, but are not limited to, dissolved oxygen, pH, turbidity or solids percentage, temperature, and conductivity. In at least one embodiment, data from the hydrometer 200 and one or more measurement probes may be combined to provide composite data such as density, corrosion rates, or scaling rates. Methods of the present disclosure include the use of the hydrometer 200 to monitor wellbore fluids in real-time and to provide predictive warnings of adverse well conditions and equipment failure.

Remedial Actions

Once adverse conditions have been identified by methods of the present disclosure, one or more remedial actions can be taken to restore one or more fluid properties to the desired specification. In at least one embodiment, data collected from the hydrometer 200 may be analyzed by a computer system and used to provide a user with recommendations of possible remedial actions. In other embodiments, multiple remedial actions can be provided by a computer system tailored to the user-provided constraints of the wellsite 100. Such limitations or constraints may exist in regards to material or tool availability, cost, timing, and the like.

Remedial actions used with the present methods and systems may include the use of any chemical additives known in the art for treating wellbore fluids. Examples of chemical additives that may be suitable include, but are not limited to, salts, brines, weighting agents, flocculants, surfactants (e.g., foamers, defoamers, emulsifiers, demulsifiers, etc.), pH adjusters (e.g., buffers, acids, bases), viscosifiers, biocides, coagulants, corrosion inhibitors, oxygen scavengers, sulfide scavengers, scale inhibitors, and any combinations thereof. In one embodiment, remedial actions may involve the addition of chemical additives under varying wellbore conditions, such as temperature, shear rate, flow rate, additive concentration, additive dosing rate, residence time (e.g., time that the additive is allowed to react with components of the wellbore fluid before other treatments are performed), and any combinations thereof. Remedial actions may include a number of treatments to control or mitigate adverse conditions that include adjusting the wellbore fluid density by introducing solid salts, brines, base fluid, or additives such as flocculants or weighting agents.

In one or more embodiments, data obtained from the hydrometer 200 may be compiled over time and used to develop algorithms to predict and or anticipate changes to the wellbore fluid conditions downhole. Predictions may allow for appropriate fluid adjustments that result in maintenance of, or increase to, operational efficiency as well as minimization of equipment failure. Data for individual wells can be formation dependent, and may include information such as but not limited to geology, total well depth, rate of penetration, as well as the downhole fluid type and weight utilized.

Embodiments disclosed herein include:

A. A method includes conveying a wellbore fluid into a container of a wellsite system, the container having a float angle hydrometer housed therein and the float angle hydrometer including a buoyant structure, and a measuring component housed within or attached to the buoyant structure. The method further including determining one or more fluid properties of the wellbore fluid with the float angle hydrometer based on an inclination of the buoyant structure within the wellbore fluid, the one or more fluid properties including at least one of density, specific gravity, or fluid level.

B. A system includes a surface wellbore fluid circulating system installed at a wellsite including a container and a wellbore fluid residing within the container. The system further including a float angle hydrometer disposed in the wellbore fluid within the container and configured to determine one or more fluid properties of the wellbore fluid.

Each of embodiments A and B may have one or more of the following additional elements in any combination: Element 1: wherein the one or more fluid properties further include at least one of dissolved oxygen, pH, turbidity, or conductivity. Element 2: further comprising undertaking a remedial action to alter at least one of the one or more fluid properties. Element 3: wherein determining the one or more fluid properties comprises obtaining multiple measurements of the wellbore fluid over a time interval. Element 4: wherein determining the one or more fluid properties comprises measuring the one or more fluid properties in real-time. Element 5: wherein the container is a suction tank included in the wellsite system. Element 6: wherein the container is a measurement tank included in the wellsite system. Element 7: wherein the measurement tank is in fluid communication with a suction tank included in the wellsite system. Element 8: further comprising undertaking a remedial action based on the one or more fluid properties determined. Element 9: wherein the remedial action comprises adjusting one or more of a density of the wellbore fluid, a pH of the wellbore fluid, an additive concentration in the wellbore fluid, a brine concentration in the wellbore fluid, and a fluid level of the wellbore fluid within the container. Element 10: wherein undertaking the remedial action comprises providing an additive or a base fluid to the wellbore fluid and thereby modifying a density of the wellbore fluid. Element 11: wherein the float angle hydrometer includes a wireless transmitter for communicating with a computer system. Element 12: wherein the measuring component is an accelerometer.

Element 13: wherein the wellbore fluid comprises a brine. Element 14: wherein the wellbore fluid has a density of 6.5 ppg or more. Element 15: further comprising a wellbore, wherein the surface wellbore fluid circulating system is in fluid communication with the wellbore. Element 16: wherein the float angle hydrometer transmits measurements to a computer system that calculates a density of the wellbore fluid. Element 17: wherein the container is a measurement tank. Element 18: wherein the container is in fluid communication with a suction tank.

By way of non-limiting example, exemplary combinations applicable to A and B include: Element 6 with Element 7; Element 8 with Element 9; Element 8 with Element 10; Element 15 with Element 18; and Element 17 with Element 18.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein.

While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

The use of directional terms such as above, below, upper, lower, upward, downward, left, right, and the like are used in relation to the illustrative embodiments as they are depicted in the figures, the upward direction being toward the top of the corresponding figure and the downward direction being toward the bottom of the corresponding figure.

We claim:

1. A method comprising:
 processing a wellbore fluid with a fluid circulating system by conveying the wellbore fluid from a fluid separation system to a suction tank and thereby generating processed wellbore fluid;
 conveying at least a portion the processed wellbore fluid from the suction tank into a measurement container, the measurement container having a float angle hydrometer housed therein;
 measuring, with the float angle hydrometer, an inclination angle of the float angle hydrometer; and
 determining one or more fluid properties of the processed wellbore fluid based on the measured inclination angle, wherein the method further comprises providing a stable environment in the measurement container while measuring of the inclination angle, wherein the stable environment lacks mechanical agitators.

2. The method of claim 1, wherein a first flow path is defined from the suction tank to a mud supply line, and a second flow path is defined from the suction tank to the measurement container, and wherein conveying at least a portion the processed wellbore fluid from the suction tank into the measurement container comprises diverting at least a portion of the processed wellbore fluid from the first flow path to the second flow path.

3. The method of claim 2, wherein conveying at least a portion the processed wellbore fluid from the suction tank into the measurement container further comprises:
 conveying the diverted portion of the processed wellbore fluid through a control valve and to the measurement container; and
 isolating, with the control valve, the measurement container from the suction tank during the measuring of the inclination angle.

4. The method of claim 3, further comprising conveying the diverted portion of the processed wellbore fluid from the measurement container back to the suction tank.

5. The method of claim 1, wherein determining the one or more fluid properties comprises obtaining multiple measurements of the wellbore fluid over a time interval.

6. The method of claim 1, wherein determining the one or more fluid properties comprises measuring the one or more fluid properties in real-time.

7. The method of claim 1, further comprising undertaking a remedial action based on the one or more fluid properties determined.

8. The method of claim 7, wherein the remedial action comprises adjusting one or more of a density of the wellbore fluid, a pH of the wellbore fluid, an additive concentration in the wellbore fluid, a brine concentration in the wellbore fluid, and a fluid level of the wellbore fluid within the measurement container.

9. The method of claim 7, wherein undertaking the remedial action comprises providing an additive or a base fluid to the wellbore fluid and thereby modifying a density of the wellbore fluid.

10. The method of claim 1, further comprising communicating the measured inclination angle to a computer system.

11. The method of claim 1, wherein measuring the inclination angle of the float angle hydrometer comprises measuring the inclination angle with an accelerometer.

12. A system, comprising:
 a surface wellbore fluid circulating system including:
  a fluid separation system;
  a suction tank fluidically coupled to the fluid separation system;
  a mud supply line fluidically coupled to the suction tank; and
  a measurement container fluidically coupled to the suction tank, wherein the measurement container lacks mechanical agitators; and
 a float angle hydrometer to be disposed in a wellbore fluid within the measurement container, the float angle hydrometer comprising:
  a housing; and
  a measurement module device operable to measure an inclination angle of the housing,
 wherein the inclination angle is indicative of one or more fluid properties of the wellbore fluid.

13. The system of claim 12, further comprising a computer system to communicate with the float angle hydrometer, the computer system being operable to:
 receive the inclination angle from the measurement module device; and
 determine a density of the wellbore fluid based on the inclination angle.

14. The system of claim 12, wherein a first flow path is defined from the suction tank to the mud supply line and a second flow path is defined from the suction tank to the measurement container, and wherein the system further comprises a control valve to divert processed wellbore fluid from the first flow path to the second flow path.

15. The system of claim 14, wherein a third flow path is defined from the measurement container to the suction tank, and wherein the divert processed wellbore fluid is to flow from the measurement container to the suction tank along the third flow path.

16. The system of claim 12, wherein the float angle hydrometer is tethered to the measurement container at a fixed depth.

* * * * *